US00PP10111P

United States Patent [19]

Trees

[11] Patent Number: Plant 10,111

[45] Date of Patent: Nov. 4, 1997

[54] NEW GUINEA IMPATIENS NAMED 'APPLE BLOSSOM'

[75] Inventor: Scott C. Trees, Arroyo Grande, Calif.

[73] Assignee: Ball Horticultural Company, West Chicago, Ill.

[21] Appl. No.: 685,673

[22] Filed: Jul. 24, 1996

[51] Int. Cl.[6] ..... A01H 5/00

[52] U.S. Cl. ..... Plt./87.6

[58] Field of Search ..... Plt./87.6

[56] References Cited

PUBLICATIONS

GTITM, UPOVROM Listing for 'Apple Blossom' on Application of Jul. 5, 1996, Oct. 31, 1996.

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'Apple Blossom' is provided. This new cultivar was the result of a controlled breeding program wherein the 'Barbados' cultivar (U.S. Plant Pat. No. 8,467) was pollinated by a plant designated '6484-1' (non-patented in the United States). The new cultivar forms large light pink flowers with a deep fuchsia eye that display an iridescent appearance. The foliage is dark green and is accented by a red midvein (as illustrated). An attractive compact upright mounded growth habit is exhibited. The new cultivar can be readily distinguished from the 'Tahiti' cultivar (U.S. Plant Pat. No. 8,601).

1 Drawing Sheet

SUMMARY OF THE INVENTION

The present invention comprises a new and distinctive Impatiens plant, botanically known as New Guinea Impatiens, and hereinafter is referred to by the cultivar name 'Apple Blossom'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was the 'Barbados' cultivar (U.S. Plant Pat. No. 8,467) which exhibits bright orange blossoms, medium green foliage with a red midvein, and a compact growth habit. The male parent (i.e., the pollen parent) was a plant designated '6484-1' (non-patented in the United States) which exhibits medium salmon blooms, and dark green foliage. The parentage of the new cultivar can be summarized as follows:

'Barbados'×'6484-1'.

The seeds resulting from the above pollination were sown and plantlets were obtained which were physically and biologically different from each other. Selective study resulted in the identification of a single plant of the new cultivar. This plant initially was designated BFP-595.

It was found that the new cultivar of the present invention:

(a) exhibits attractive large light pink flowers with a deep fuchsia eye,
(b) forms dark green foliage with a reddish midvein,
(c) exhibits a good basal branching character, and
(d) exhibits a compact upright mounded growth habit.

Plants of the new variety can be grown close together in the greenhouse. Also, the new cultivar performs well in the garden where it is free-flowering.

Asexual reproduction of the new cultivar by terminal or stem cuttings taken during 1993, at Arroyo Grande, Calif., U.S.A. has demonstrated that the characteristics of the new cultivar as herein described are firmly fixed and are retained through successive generations of such asexual propagation.

The 'Apple Blossom' cultivar has not been observed under all possible environmental conditions to date. Accordingly, it is possible that the phenotype may vary somewhat with variations in the environment, such as temperature, light intensity, and day length.

When the new cultivar of the present invention is compared to the parent 'Tahiti' cultivar (U.S. Plant Pat. No. 8,601), it is found that the new variety exhibits larger flowers of a brighter pink, and somewhat smaller foliage.

Plants of the new cultivar are marketed under the CELEBRETTE trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is The R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Botanical classification: *Impatiens hawkeri.*

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Compact upright mounded. Internode lengths of approximately 1.5 to 2.3 cm. commonly are exhibited. A mature plant commonly measures approximately 6.5 to 7.5 cm. in height and approximately 14 to 16 cm. in width. This compares to a height of approximately 9 to 10 cm. and a width of approximately 18 to 20 cm. for the parent 'Tahiti' cultivar.

*Foliage.*—The configuration is elliptic with an acuminate apex and an acuminate base. The mature leaves of the new cultivar measure approximately 8.1 to 9 cm. in length×approximately 2.8 to 3 cm. in maximal width compared to approximately 9 to 11 cm. in length×approximately 4 to 5 cm. in maximal width for the 'Tahiti' cultivar. The leaf margins are serrate (as illustrated). The mature foliage of new cultivar is Yellow-Green Group 147A (adaxial), and Greyed-Green Group 191B with a midvein of Greyed-Purple Group 183C (abaxial). The mature foliage coloration of the new cultivar is substantially the same as that of the 'Tahiti' cultivar. The stem coloration is Greyed-Purple Group 183C for both the new cultivar, and the 'Tahiti' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—The outer edges of the petals are Red-Purple Group 62A with veins of Red-Purple Group 63B giving an overall appearance of near Red-Purple Group 62B which commonly fades to Red-Purple Group 62D at the center with Red-Purple Group 63A at the base of all petals forming an eye (adaxial), and veins and midrib of Red-Purple Group 63B on a background of Red-Purple Group 62B generally giving an overall appearance of Red-Purple Group 62A (abaxial). This compares to Red-Purple Group 62C (adaxial), and Red-Purple Group 65B (abaxial) for the 'Tahiti' cultivar.

*Quantity of flowers.*—Approximately 4 to 5 per axil which can be compared to approximately 3 to 4 per axil for the 'Tahiti' cultivar.

*Number of petals.*—Five, and overlapping.

*Petal shape.*—Heart-shaped, with the upper three petals commonly having broader bases than the lower two petals.

*Flower size.*—Approximately 6 to 6.7 cm. in length and approximately 5.5 to 6.6 cm. in width. This can be compared to approximately 5.8 to 6 cm. in length and approximately 5.8 to 6 cm. in width for the 'Tahiti' cultivar.

*Flower buds.*—Ellipsoidal in configuration, and generally covered with three sepals plus two rudimentary sepals fused into the under surface of the superior petal. A spur originating from the base of the inferior sepal is approximately 4 to 5 cm. in length on fully opened flowers which can be compared to approximately 5 to 5.5 cm. for the spur length of the 'Tahiti' cultivar.

*Reproductive organs.*—The stamens are Red-Purple Group 63A at the base and White Group 155D at the outer edge for both the new cultivar and the 'Tahiti' cultivar. The anthers tend to be fused together forming one organ that surrounds the pistil. Commonly the anthers shed pollen prior to the stigma becoming receptive. The pollen coloration is Yellow Group 13D and the ovary coloration is Green Group 143C. Such pollen and ovary coloration is substantially the same as that of the 'Tahiti' cultivar.

I claim:

1. A new and distinct cultivar of New Guinea Impatiens plant named 'Apple Blossom', substantially as herein shown and described, which:

(a) exhibits attractive large light pink flowers with a deep fuchsia eye,
(b) forms dark green foliage with a reddish midvein,
(c) exhibits a good basal branching character, and
(d) exhibits a compact upright mounded growth habit.

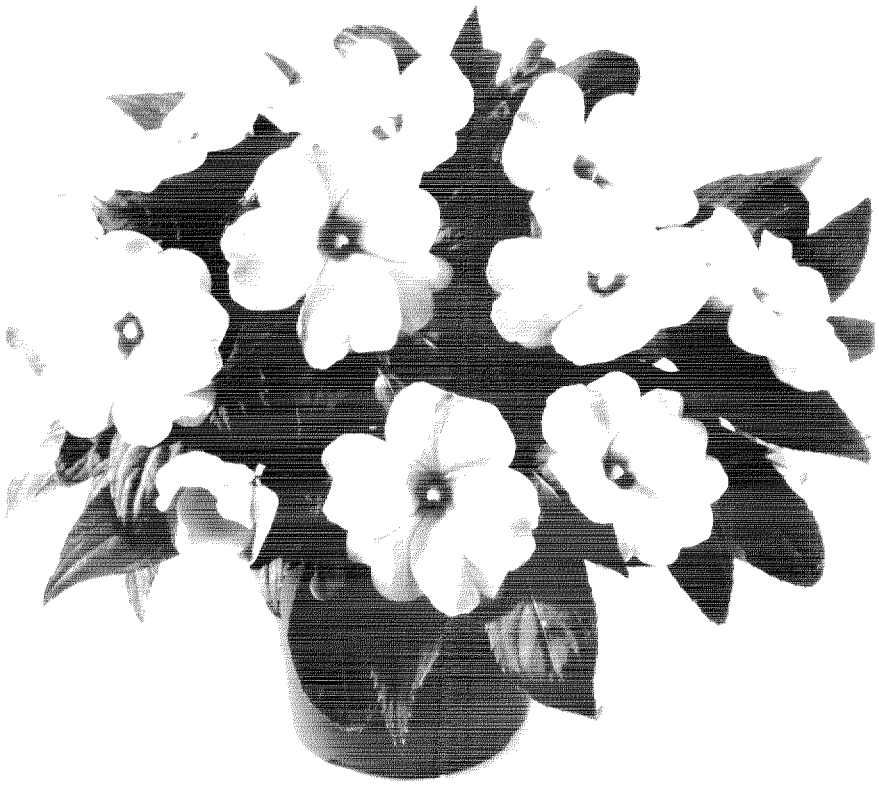

* * * * *